United States Patent [19]

Yoneoka et al.

[11] 4,232,171

[45] Nov. 4, 1980

[54] PROCESS FOR PRODUCING METHYL FORMATE

[75] Inventors: Mikio Yoneoka; Minoru Osugi; Takeo Ikarashi, all of Niigata, Japan

[73] Assignee: Mitsubishi Gas Chemical Company, Inc., Tokyo, Japan

[21] Appl. No.: 28,681

[22] Filed: Apr. 10, 1979

[30] Foreign Application Priority Data

Apr. 21, 1978 [JP] Japan .................................. 53-47436

[51] Int. Cl.$^2$ ....................... C07C 67/40; C07C 69/06
[52] U.S. Cl. ................................. 560/239; 252/455 R
[58] Field of Search ...................... 560/239; 252/455 R

[56] References Cited

U.S. PATENT DOCUMENTS

| 1,975,853 | 10/1934 | Lazier | 560/239 |
| 2,004,350 | 6/1935 | Scott | 560/239 |
| 2,504,497 | 4/1950 | Charles et al. | 560/239 |

Primary Examiner—Vivian Garner
Attorney, Agent, or Firm—Frishauf, Holtz, Goodman & Woodward

[57] ABSTRACT

A process for producing methyl formate which comprises dehydrogenating methanol in the vapor phase in the presence of a catalyst containing copper and a cement is disclosed.

10 Claims, No Drawings were crushed to ⅛th the tablet size. The resulting particles were charged in a pyrex glass pipe having 20 mm inner diameter, and were maintained at 200° C. for 6 hrs. in a stream of hydrogen to reduce the copper compound.

A reactor having 20 mm inner diameter was filled with 10 ml of the activated catalyst, and methanol vapor was charged at a space velocity of 3700 $hr^{-1}$. The reaction was continuously carried out at an atmospheric pressure at 235° C. for 52 hours. The results are shown in Table 1.

TABLE 1

| | Number of hours from the start of the reaction | | | |
|---|---|---|---|---|
| | 1 | 24 | 30 | 52 |
| Conversion of methanol mol % | 36.9 | 34.2 | 32.6 | 31.8 |
| Selectivity to methyl formate mol % | 88.7 | 91.0 | 91.9 | 92.3 |
| Yield of methyl formate mol % | 32.7 | 31.1 | 30.0 | 29.4 |

EXAMPLE 2

The basic copper carbonate prepared in Example 1 and high alumina cement and Alumina Cement No. 2 (calcium-aluminate cement) produced by Denki Kagaku Kogyo Kabushiki Kaisha were used in the proportions as given in Table 2. The activated catalysts were prepared by following the procedure of Example 1 except that the reaction temperature and space velocity of methanol as given in Table 2 were employed. The results are shown in Table 2.

TABLE 2

| Kinds of cement | Grams of cement per 1 gram-atom of copper | Reaction Temperature (°C.) | Space Velocity of methanol ($hr^{-1}$) | | Number of hours from start of the reaction | | | |
|---|---|---|---|---|---|---|---|---|
| | | | | | 1 | 30 | 50 | 75 |
| High alumina cement | 44.2 | 260 | 3700 | Conversion of methanol mol. % | 48.6 | 35.5 | | |
| | | | | Selectivity to methyl formate mol. % | 77.1 | 85.2 | | |
| | | | | Yield of methyl formate mol. % | 37.5 | 30.2 | | |
| High alumina cement | 22.1 | 256 | 3700 | Conversion mol % | 49.9 | 38.9 | 35.7 | 33.7 |
| | | | | Selectivity mol. % | 74.9 | 84.9 | 86.4 | 87.1 |
| | | | | Yield mol. % | 37.4 | 33.0 | 30.8 | 29.4 |
| High alumina cement | 11.1 | 260 | 3800 | Conversion mol. % | 50.7 | 38.7 | 34.9 | 30.6 |
| | | | | Selectivity mol. % | 78.9 | 86.4 | 87.6 | 88.7 |
| | | | | Yield mol. % | 40.0 | 33.4 | 30.6 | 27.1 |
| Alumina cement No. 2 | 22.1 | 259 | 3800 | Conversion mol. % | 50.8 | 39.8 | 35.3 | |
| | | | | Selectivity mol. % | 74.0 | 84.7 | 85.2 | |
| | | | | Yield mol. % | 37.6 | 33.7 | 30.1 | |

COMPARATIVE EXAMPLE 1

The basic copper carbonate prepared in Example 1, and commercially available calcium oxide and silica sol were used as the catalyst components. These components were mixed in such a proportion that atomic ratio of Cu:Ca:Si was 1:0.3:0.3. The activated catalyst was prepared from the mixture in the same way as in Example 1.

Methanol was dehydrogenated by using the catalyst at space velocity of 3700 $hr^{-1}$ for 8 hours. Therefore, the activity of the catalyst was measured at the temperatures as given in Table 3. The results are shown in Table 3.

TABLE 3

| | Reaction Temperature (°C.) | | | | |
|---|---|---|---|---|---|
| | 192 | 207 | 218 | 232 | 246 |
| Conversion of methanol mol % | 27.0 | 33.8 | 39.3 | 46.3 | 52.5 |
| Selectivity to methyl formate mol % | 68.1 | 57.2 | 51.4 | 46.9 | 42.7 |
| Yield of methyl formate mol % | 18.4 | 19.4 | 20.2 | 21.7 | 22.7 |

What we claim is:

1. In the process for preparing methyl formate by dehydrogenating methanol by contacting methanol with a copper-containing catalyst in the vapor phase, the improvement comprising utilizing as the copper-containing catalyst, a catalyst comprising copper and a cement selected from the group consisting of Portland cement, calcium-aluminate cement and mixtures thereof.

2. The process of claim 1 in which 5 to 150 grs. of the cement is used per gram-atom of copper.

3. The process of claim 1 in which 5 to 100 grs. of the cement is used per gram-atom of copper.

4. The process of claim 1 in which 10 to 50 grs. of the cement is used per gram-atom of copper.

5. The process of claim 1 or claim 4 in which the catalyst obtained by baking a mixture of basic copper carbonate and the cement is used.

6. The process of claim 1 or claim 4 in which the dehydrogenation is carried out at a temperature in the range of from 100° C. to 400° C.

7. The process of claim 1 or claim 4 in which the dehydrogenation is carried out at a space velocity of methanol in the range of from 100 $hr^{-1}$ to 50,000 $hr^{-1}$.

ature is made uniform by kneading the paste. The mixture is baked a temperature within the range of from 250° C. to 450° C. in air or a nitrogen gas and the baked mixture is chemically reduced at a temperature within the range of from 140° C. to 400° C. in a hydrogen gas or a carbon monoxide gas to activate it.

PROCESS FOR PRODUCING METHYL FORMATE

BACKGROUND OF THE INVENTION

This invention relates to a process for producing methyl formate which comprises dehydrogenating methanol in the vapor phase in the presence of a catalyst.

A process for producing methyl formate which comprises dehydrogenating methanol in the presence of a certain catalyst was known. Examples of known catalysts are copper (French Patent No. 673,337), catalyst obtained by reducing oxides of copper, nickel, chrome and iron (U.S. Pat. No. 1,400,195) and catalyst obtained by treating a copper-aluminum alloy with an aqueous alkaline solution (U.S. Pat. No. 2,504,497). However, these patents do not disclose the yield of methyl formate obtained.

Recently developed processes for producing methyl formate include dehydrogenating methanol in the presence of a catalyst composed of copper oxide and an oxide of an element of Group IIIa or IVb of the periodic table [Japanese Patent Publication (laid open) No. 65708/1976], or use of a catalyst composed of copper oxide and an oxide of aluminum or silicon selected from the group consisting of silica, silica alumina treated with an alkali and alumina treated with an alkali [Japanese Patent Publication (laid open) No. 63117/1976]. According to these processes, when conversion of methanol is raised, selectivity to methyl formate is lowered. So, according to these processes, in order to improve selectivity to methyl formate, conversion of methanol must be suppressed. The yield of methyl formate is the product of (a) the selectivity to methyl formate and (b) the conversion of methanol. Therefore, methyl formate can not be obtained in a high yield, according to these processes.

SUMMARY OF THE INVENTION

The present inventors have carried out research for increasing the yield of methyl formate. As a result, we found that when methanol is dehydrogenated in the presence of a catalyst containing copper and a cement, methyl formate can be obtained in a high yield.

Therefore, an object of this invention is to provide a process for producing methyl formate from methanol in a high yield.

DETAILED DESCRIPTION OF THE INVENTION

The catalyst employed in this invention contains copper and a commercially available cement.

A variety of copper compounds can be used as the copper component constituting the catalyst. Examples of the copper compounds include hydroxide, oxides, carbonate, inorganic acid salts and organic acid salts of copper. Particularly, basic copper carbonate is preferred as the copper compound.

Examples of the cements include portland cement, calcium-aluminate cement (it is also called aluminous cement or high alumina cement), slag cement, trass cement and mixtures thereof. Portland cement, calcium-aluminate cement and mixture thereof are preferred as the cements.

Five to 150 grs. preferably 5 to 100 grs. of the cement may be used per gram-atom of copper, with 10 to 50 grs. of the cement per gram-atom of copper being most preferred. Outside the above range, it is necessary to raise the reaction temperature. This promotes deterioration of the catalyst.

The process for preparing the catalyst is not critical. The preferred process for preparing the catalyst is in the following: Water is added to the mixture of the copper compound and the cement to form paste, and the mixture is made uniform by kneading the paste. The mixture is baked a temperature within the range of from 250° C. to 450° C. in air or a nitrogen gas and the baked mixture is chemically reduced at a temperature within the range of from 140° C. to 400° C. in a hydrogen gas or a carbon monoxide gas to activate it.

The dehydrogenating of methanol is carried out by contacting the catalyst with methanol in the vapor phase to produce methyl formate. The reaction conditions depend on the kind of catalyst employed. Conveniently, the reaction temperature may be in the range of from about 100° C. to about 400° C., preferably from about 150° C. to about 300° C.; and space velocity of methanol may be in the range of from about 100 hr$^{-1}$ to about 50,000 hr$^{-1}$, preferably from about 500 hr$^{-1}$ to about 30,000 hr$^{-1}$; and the reaction may be carried out at an atmospheric pressure or a superpressure. About 0.1 mol to about 2 mol of a dilution gas, such as hydrogen, carbon monoxide or nitrogen which is non-active to the reaction may be present in the reaction system per 1 mol of methanol.

The process for preparing the catalyst is easy, and the resulting catalyst is stable for a long time. As one component constituting the catalyst is cement, the resulting catalyst is cheap. Furthermore, when methanol is dehydrogenated in the presence of the catalyst, methyl formate can be obtained in a high yield. Therefore, the present process is industrially valuable.

The present invention is further illustrated by the following Examples. However, this invention should not be limited by these examples, and changes and modification within the spirit and scope of this invention can be effected.

Parts and percent are by weight in the following Examples, unless otherwise specified.

EXAMPLE 1

1 Mol of reagent grade (GR) copper nitrate and 1.17 mol of reagent grade (GR) anhydrous sodium carbonate were dissolved in 1 liter of deionized water separately. The two solutions were heated to 70° C. and were mixed with each other with strong stirring, and the resulting mixture was stirred while maintaining it at 70° C. for one and half hours. The resulting mixture was allowed to stand for one hour with stirring. The precipitate was suction-filtrated from the mixture. The resulting cake was sufficiently washed with 20 liters of deionized water and was dried at 70° C. overnight.

The basic copper carbonate prepared above was mixed with portland cement produced by Sumitomo Cement Co., Ltd. so that the proportion of the portland cement used was 22.1 grs. per 1 gram-atom of copper. Water was added to the mixture to form a paste. The paste was blended and was kneaded by a kneader for 30 minutes, and was allowed to stand at 70° C. overnight. The resulting dried mixture was crushed into pieces of 2 mm to 5 mm average diameter. The pieces were baked at 390° C. for one and half hours in air. Three percent by weight of graphite was added to the mixture on the basis of the baked mixture. The mixture was shaped into tablets 6 mm in diameter and 5 mm high. The tablets 8. The process of claim 1 in which the dehydrogenation is carried out in the presence of a non-active dilution gas.

9. The process of claim 1 in which the dehydrogenation is carried out at a space velocity of methanol in the range of from 500 hr$^{-1}$ to 30,000 hr$^{-1}$.

10. The process of claim 1 in which the dehydrogenation is carried out at a temperature in the range of from 150° C. to 300° C.

* * * * *